(12) United States Patent
Mukai et al.

(10) Patent No.: US 7,754,627 B2
(45) Date of Patent: Jul. 13, 2010

(54) STRETCHABLE NON-WOVEN FABRIC, ABSORBENT ARTICLE AND ABSORBENT ARTICLE MANUFACTURING METHOD

(75) Inventors: Hirotomo Mukai, Kagawa (JP); Tatsuya Hashimoto, Kagawa (JP); Tomoko Tsuji, Kagawa (JP); Akiyoshi Kinoshita, Kagawa (JP); Hidefumi Goda, Kagawa (JP); Masaharu Tomioka, Kagawa (JP); Shinji Noma, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 188 days.

(21) Appl. No.: 11/951,674

(22) Filed: Dec. 6, 2007

(65) Prior Publication Data

US 2008/0139067 A1 Jun. 12, 2008

(30) Foreign Application Priority Data

Dec. 8, 2006 (JP) ............................. 2006-331243

(51) Int. Cl.
*D04H 1/00* (2006.01)
*D04H 13/00* (2006.01)
*D04H 3/00* (2006.01)
*D04H 5/00* (2006.01)

(52) U.S. Cl. ................... 442/328; 442/329; 264/288.8; 156/60; 156/62; 156/160; 156/161; 156/229

(58) Field of Classification Search ................. 442/328, 442/329; 264/210.7, 235.6, 288.8, 291; 156/60, 156/62, 160, 161, 229
See application file for complete search history.

(56) References Cited

U.S. PATENT DOCUMENTS 4,747,846 A 5/1988 Boland et al.

FOREIGN PATENT DOCUMENTS

| EP | 1589140 A1 * | 10/2005 |
|---|---|---|
| JP | 1503473 | 11/1989 |
| JP | 2001252306 | 9/2001 |
| JP | 2001328191 | 11/2001 |
| JP | 2004244791 | 9/2004 |
| JP | 2005058755 | 3/2005 |
| WO | WO 01/39709 A1 * | 6/2001 |

* cited by examiner

*Primary Examiner*—Norca L Torres-Velazquez
(74) *Attorney, Agent, or Firm*—Morrison & Foerster LLP

(57) ABSTRACT

The present invention provides an absorbent article imparting superior comfort during wearing without inhibiting an absorbent property of an absorbent body, and a manufacturing method thereof. In the stretchable non-woven fabrics composed of a stretchable thermoplastic fiber and a heat-adhesive fiber having a lower melting point than that of the thermoplastic fiber which is arranged on a skin non-contacting side of a chassis, a low-stretchability portion is formed, in which the stretchability of the stretchable non-woven fabrics is lowered, at least in a portion thereof which overlaps an absorbent body in a thickness direction. The low-stretchability portion is formed by heating and pressurizing the portion of an elasticized non-woven fabric being extended.

8 Claims, 9 Drawing Sheets

STRETCHABLE NON-WOVEN FABRIC, ABSORBENT ARTICLE AND ABSORBENT ARTICLE MANUFACTURING METHOD

This application is based on and claims the benefit of priority from Japanese Patent Applications No. 2006-331243, filed on 8 Dec. 2006, the content of which is incorporated herein by reference.

BACKGROUND OF THE INVENTION

1. Field of the Invention

The present invention relates to stretchable non-woven fabric, absorbent articles such as disposable diapers and an absorbent article manufacturing method.

2. Related Art

The conventional disposable diaper is designed to have stretchability to follow the movement of a wearer's body and to adhere to various body shapes. However, this stretchability could make wrinkles on an absorbent body and a gap between the absorbent body and the wearer's body. Such a displacement leads to leakage of the discharged matter.

In contrast, a disposable diaper is disclosed in, for example, Japanese Translation of PCT International Publication, Publication No. H01-503473 (hereinafter referred to as "Patent Document 1") which includes a stretchable member on an outer cover, in which an insert, with an absorbent body arranged in the center, is connected to front and back trunk flap portions on the outer cover only by both lengthwise end portions thereof, thus not inhibiting the stretchability of the outer cover, following the wearer's body shape and optimizing a capability of an absorbent body.

However, in the disposable diaper of Patent Document 1, an insert, with an absorbent body arranged in the center, is connected to trunk flap portions only by both lengthwise end portions thereof. Thus, the insert is arranged while being spaced apart from a chassis. This means that the absorbent body cannot be stretched out and can easily be twisted.

SUMMARY OF THE INVENTION

The objective of the present invention is to provide a non-woven fabric, an absorbent article and an absorbent article manufacturing method that inhibit unnecessary deformation of an absorbent body, such as twisting.

According to a first aspect of the present invention, a stretchable non-woven fabric is provided including a stretchable thermoplastic fiber and heat-adhesive fibers having a lower melting point than that of the thermoplastic fiber, having a low-stretchability region of a lower stretchability than that of a circumference thereof, in which at least the heat-adhesive fibers are fused to each other, in a predetermined area.

According to a second aspect of the stretchable non-woven fabric as described in the first aspect of the present invention, the low-stretchablity region is air-permeable.

According to a third aspect of the present invention, a manufacturing method of a stretchable non-woven fabric having a region of lower stretchability is provided including a process of lowering a stretchability of a predetermined area in a stretchable non-woven fabric including a stretchable thermoplastic fiber and heat-adhesive fibers having a lower melting point than that of the thermoplastic fiber, in which at least the heat-adhesive fibers are fused to each other in the predetermined area.

According to a fourth aspect of the manufacturing method of the stretchable non-woven fabric as described in the third aspect of the present invention, the process of lowering stretchability includes a step extending the stretchable non-woven fabric before the step of fusing the heat-adhesive fibers each other.

According to a fifth aspect of the present invention, a manufacturing method of a stretchable composite sheet is provided including: a non-woven fabric extending process in which a stretchable non-woven fabric including a stretchable thermoplastic fiber and heat-adhesive fibers having a lower melting point than that of the thermoplastic fiber is stretched at a predetermined stretching rate selected from a range of 20 to 200%; a composite sheet forming process in which the non-woven fabric, which is extended in the non-woven fabric extending process, is adhesively laminated to a non-stretchable sheet to obtain a composite sheet; and a process of lowering stretchability in which a stretchability of a predetermined area in the composite sheet is lowered to less than that of a circumference thereof, by fusing at least the heat-adhesive fibers in the predetermined area to each other.

According to a sixth aspect of the present invention, a absorbent article having a width direction and a lengthwise direction orthogonal to the width direction is provided, including: a front trunk region; a rear trunk region; a chassis with a crotch arranged between the front trunk region and the rear trunk region; and an absorbent body arranged along the lengthwise direction in which at least a portion thereof overlaps the chassis in a thickness direction, in which a stretchable non-woven fabric including a stretchable thermoplastic fiber and heat-adhesive fibers having a lower melting point than that of the thermoplastic fiber is arranged in at least a portion of the chassis, a low-stretchability region, having a lower stretchability than that of a circumference thereof, is formed in a predetermined region of the stretchable non-woven fabric, and a stretchability of a thermoplastic fiber in the low-stretchability region is inhibited by a fusion structure in which the heat-adhesive fibers in the low-stretchability region are fused to each other.

According to a seventh aspect of the absorbent article as described in the sixth aspect of the present invention, the low-stretchability region is formed substantially in a center in the width direction of the front trunk region and the rear trunk region, and overlaps in the thickness direction at least both of the side edges in the width direction of the absorbent body.

According to an eighth aspect of the absorbent article as described in the sixth or seventh aspect of the present invention, the low-stretchablity region is air-permeable.

According to the present invention, a non-woven fabric, an absorbent article and an absorbent article manufacturing method can inhibit unnecessary deformation of an absorbent body, such as twisting.

DETAILED DESCRIPTION OF THE INVENTION

Preferred embodiments of the present invention are described below. Embodiments of the present invention are described below with reference to the accompanying drawings. However, it is to be understood that the embodiments of the present invention are not limited to the following, and the technical scope of the present invention is not limited thereto.

Figure 1:
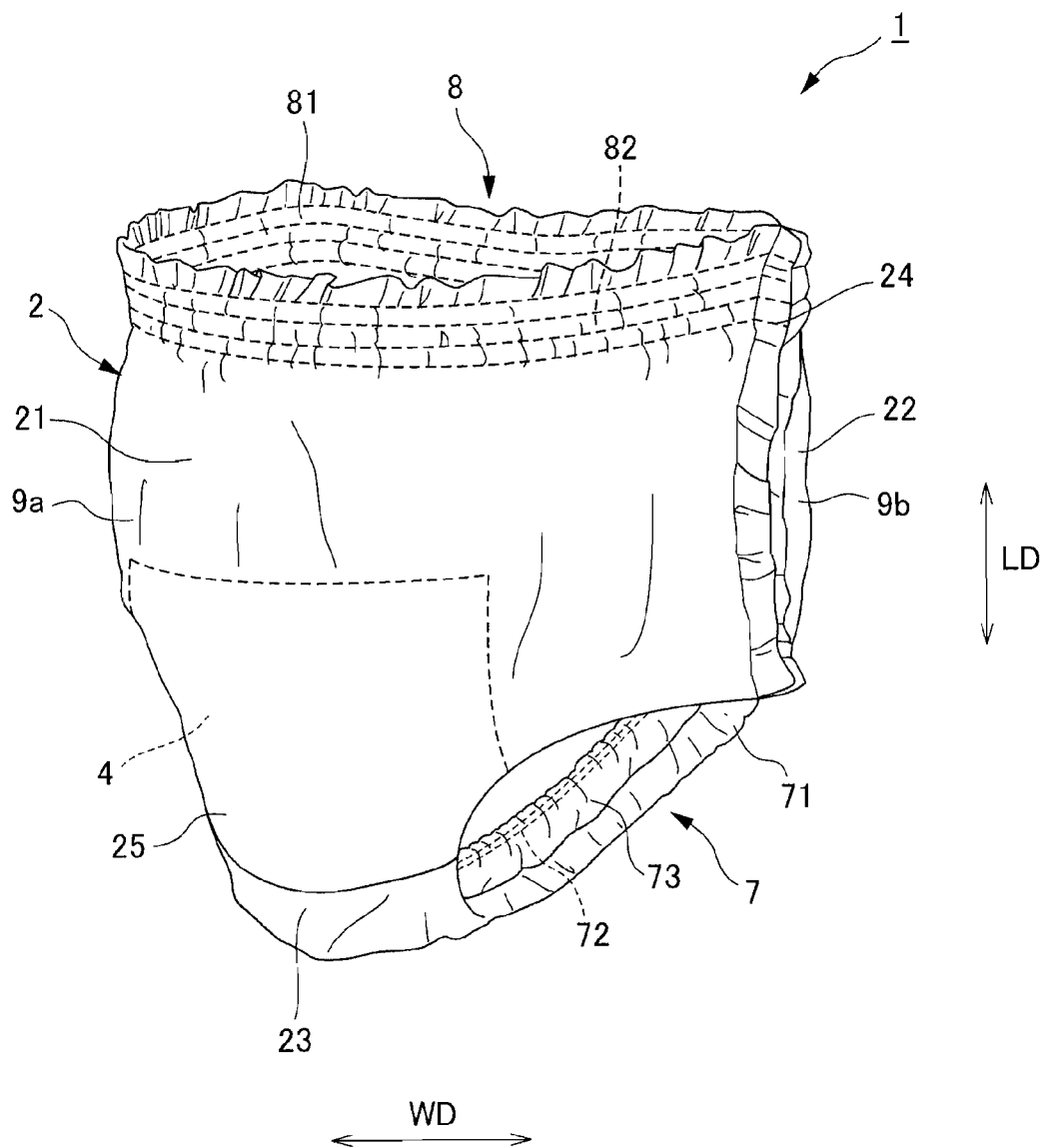
FIG. 1 is a perspective view showing a disposable diaper in the first embodiment of the present invention.
Figure 2:
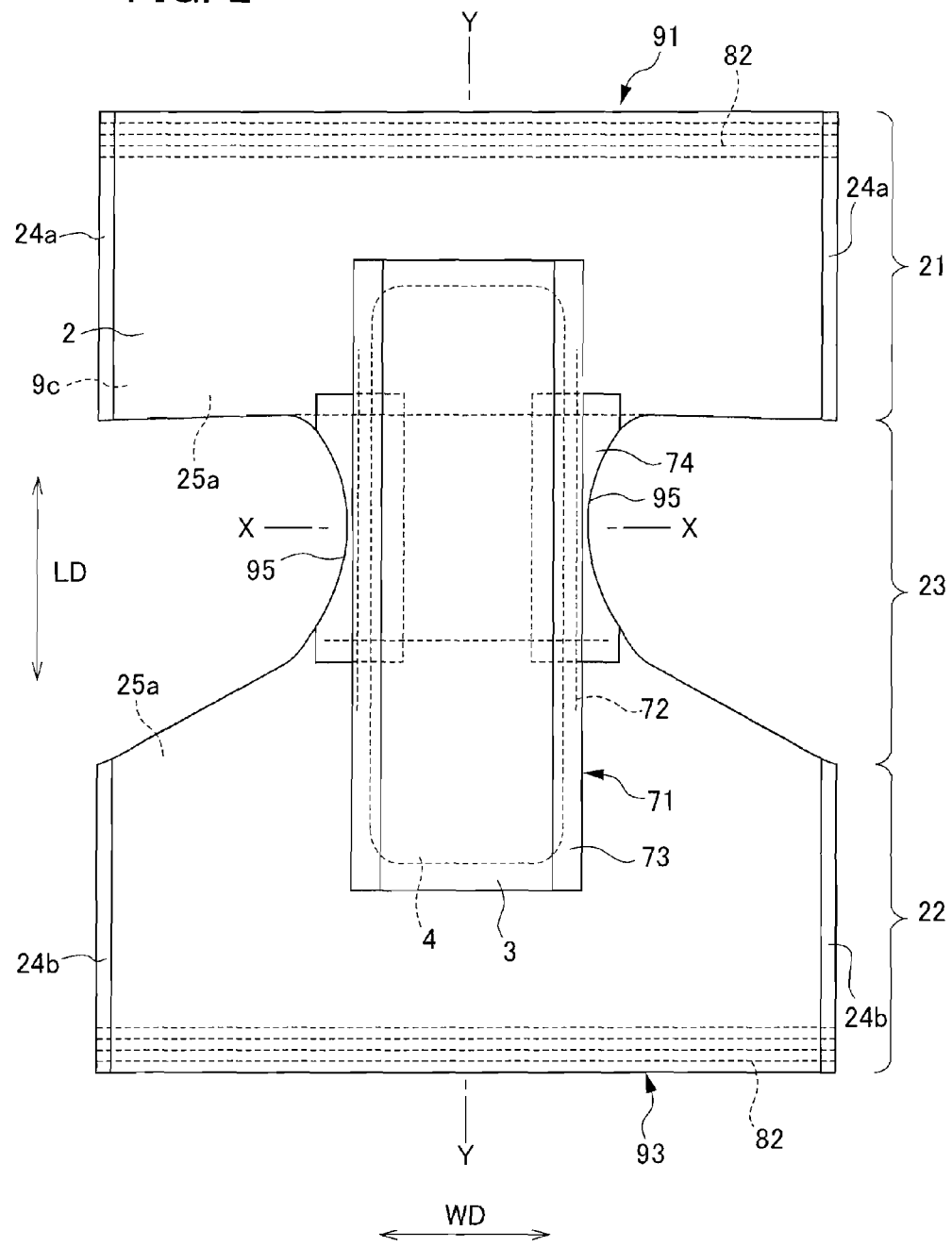
FIG. 2 is a developed view showing a disposable diaper in a first embodiment of the present invention in the expanded state.
Figure 3:
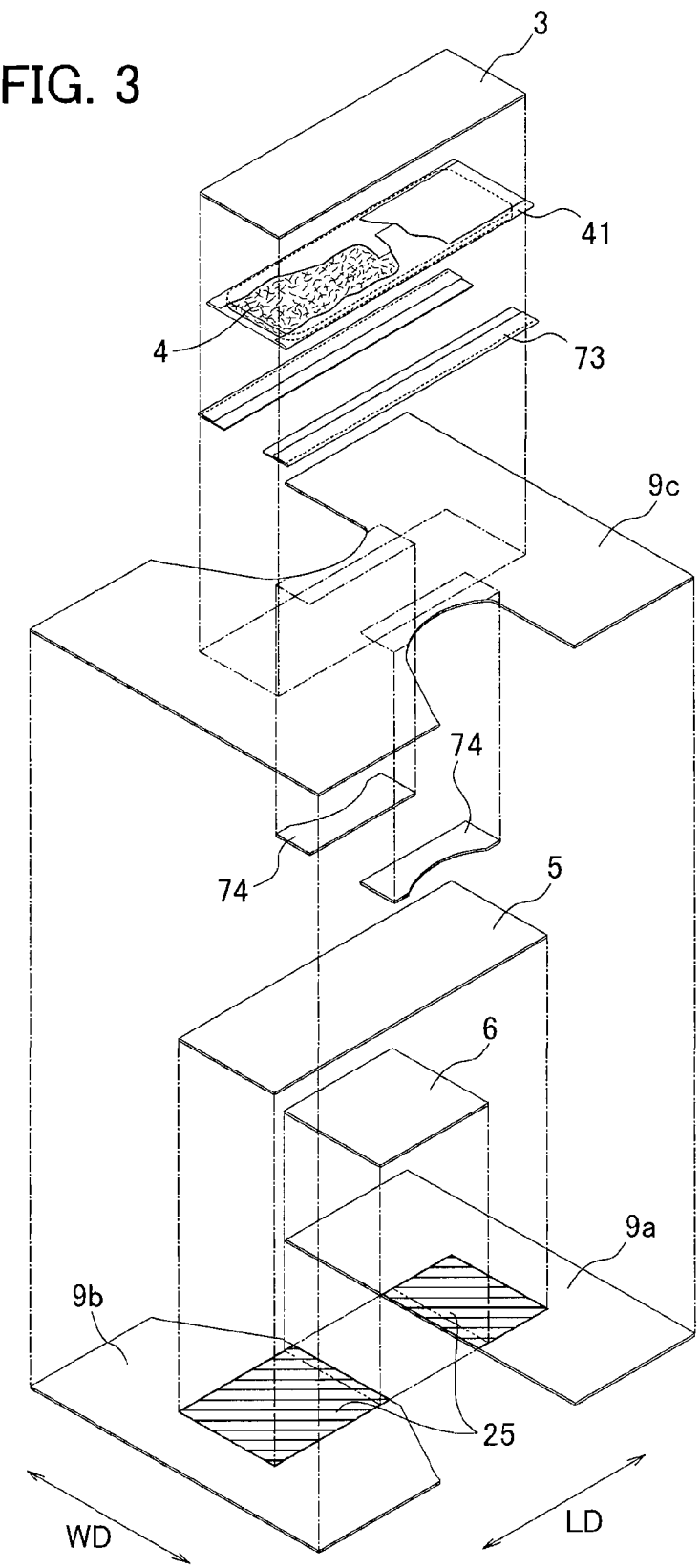
FIG. 3 is a perspective exploded view showing a disposable diaper in the first embodiment of the present invention.
Figure 4:
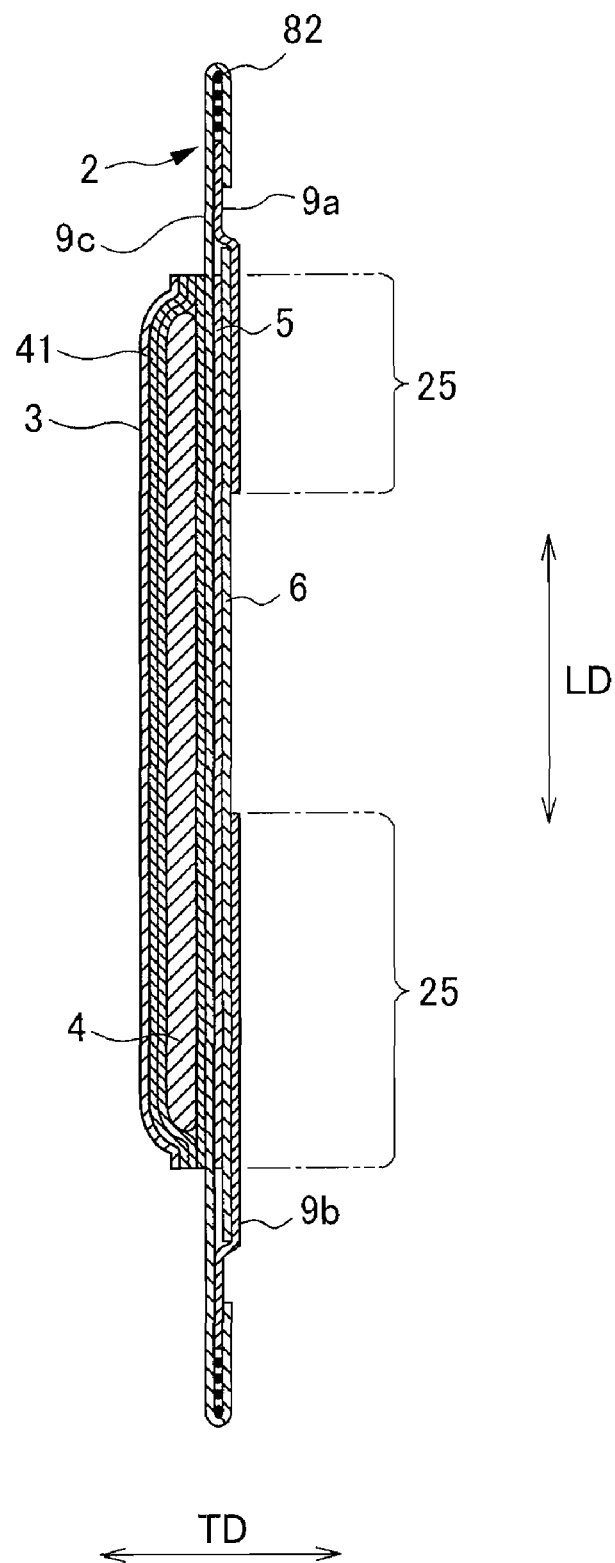
FIG. 4 is a sectional view taken along the line Y-Y in FIG. 2.
Figure 5:
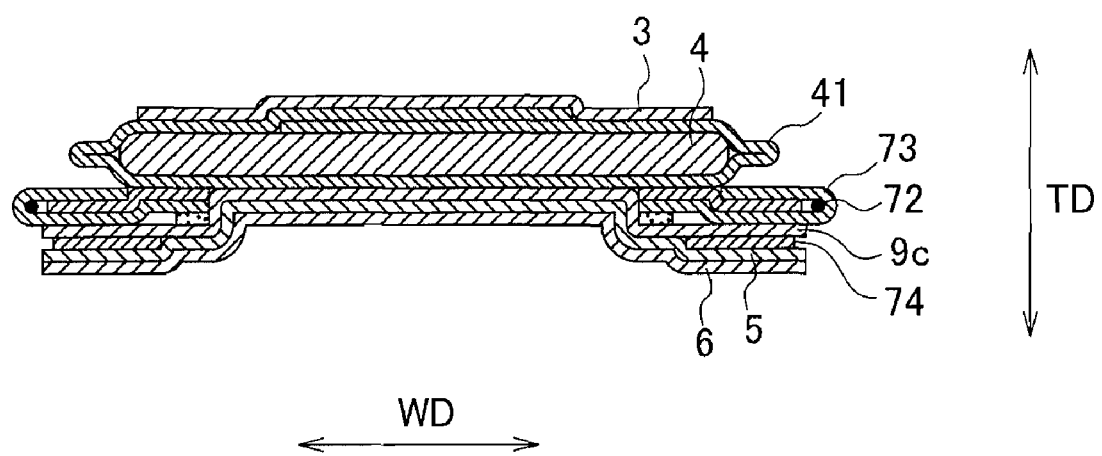
FIG. 5 is a sectional view taken along the line X-X in FIG. 2.
Figure 6A:
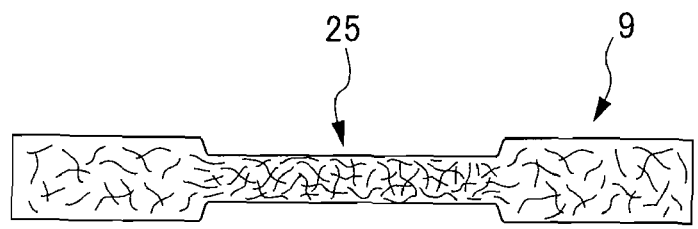
FIG. 6A is a cross-sectional view showing a low-stretchability region in the first embodiment of the present invention.
Figure 6B:
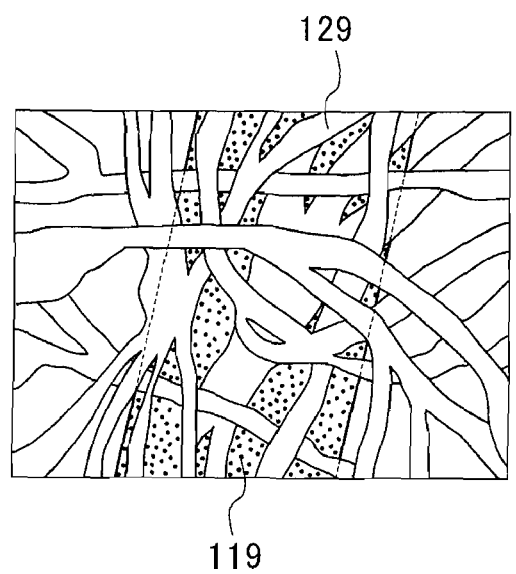
FIG. 6B is a partially enlarged view of the low-stretchability region of FIG. 6A.
Figure 7:
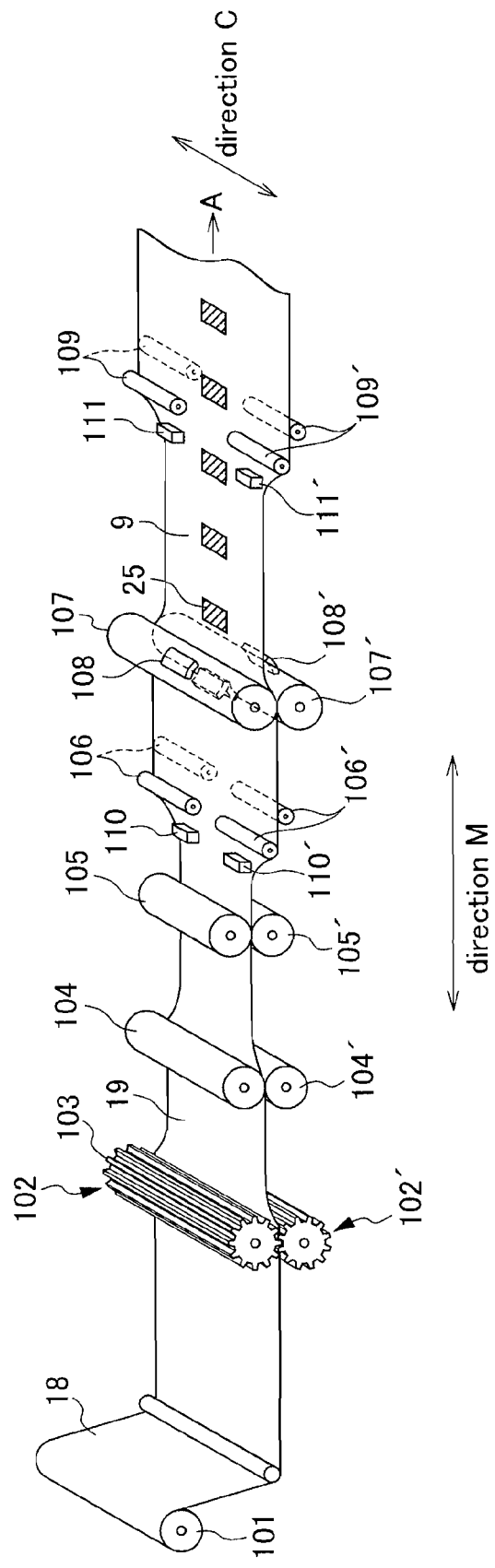
FIG. 7 is a diagram illustrating a stretchable non-woven fabric manufacturing process in the first embodiment of the present invention.
Figure 8:
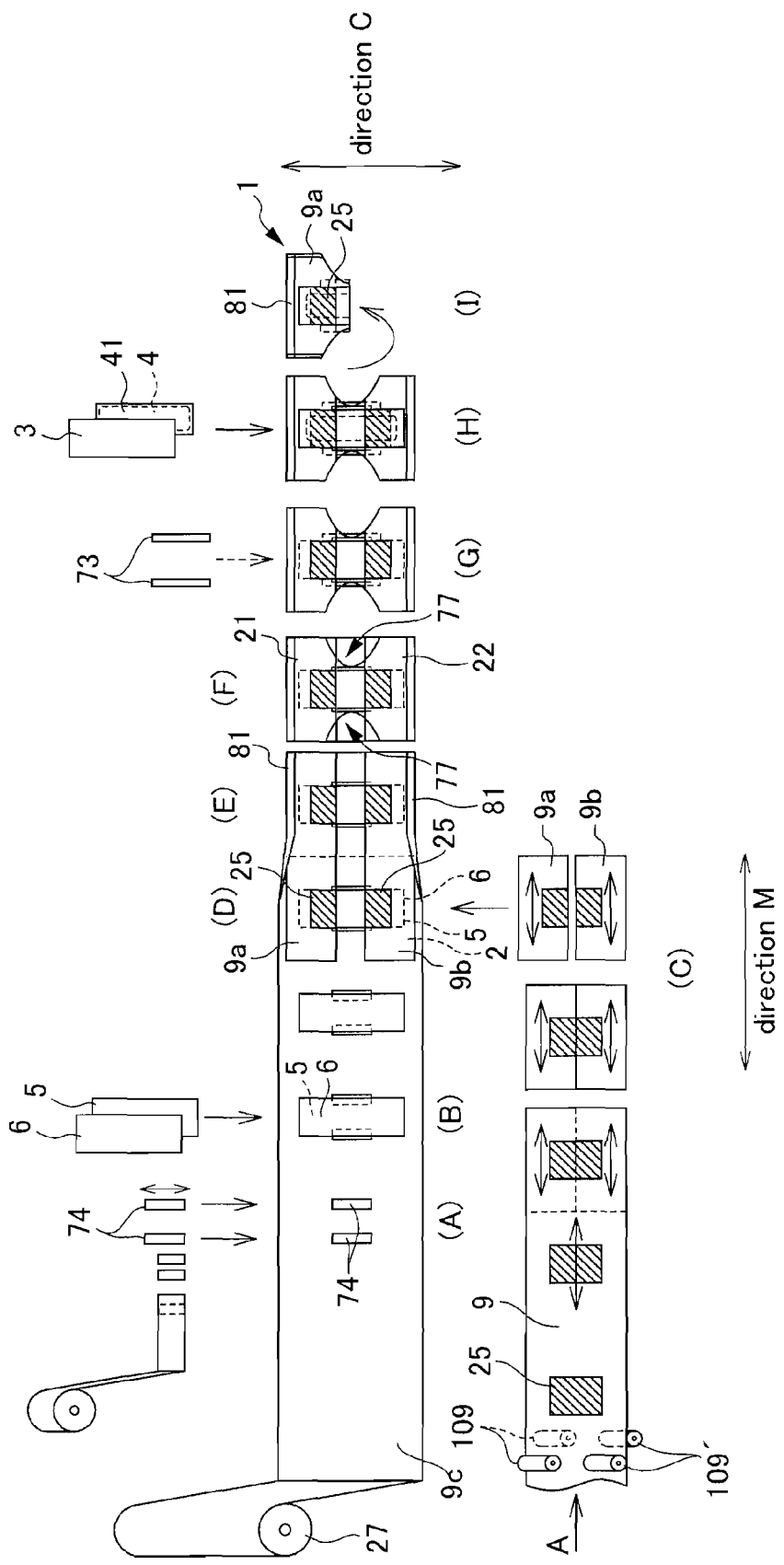
FIG. 8 is a diagram illustrating an absorbent article manufacturing process in the first embodiment of the present invention.
Figure 9:
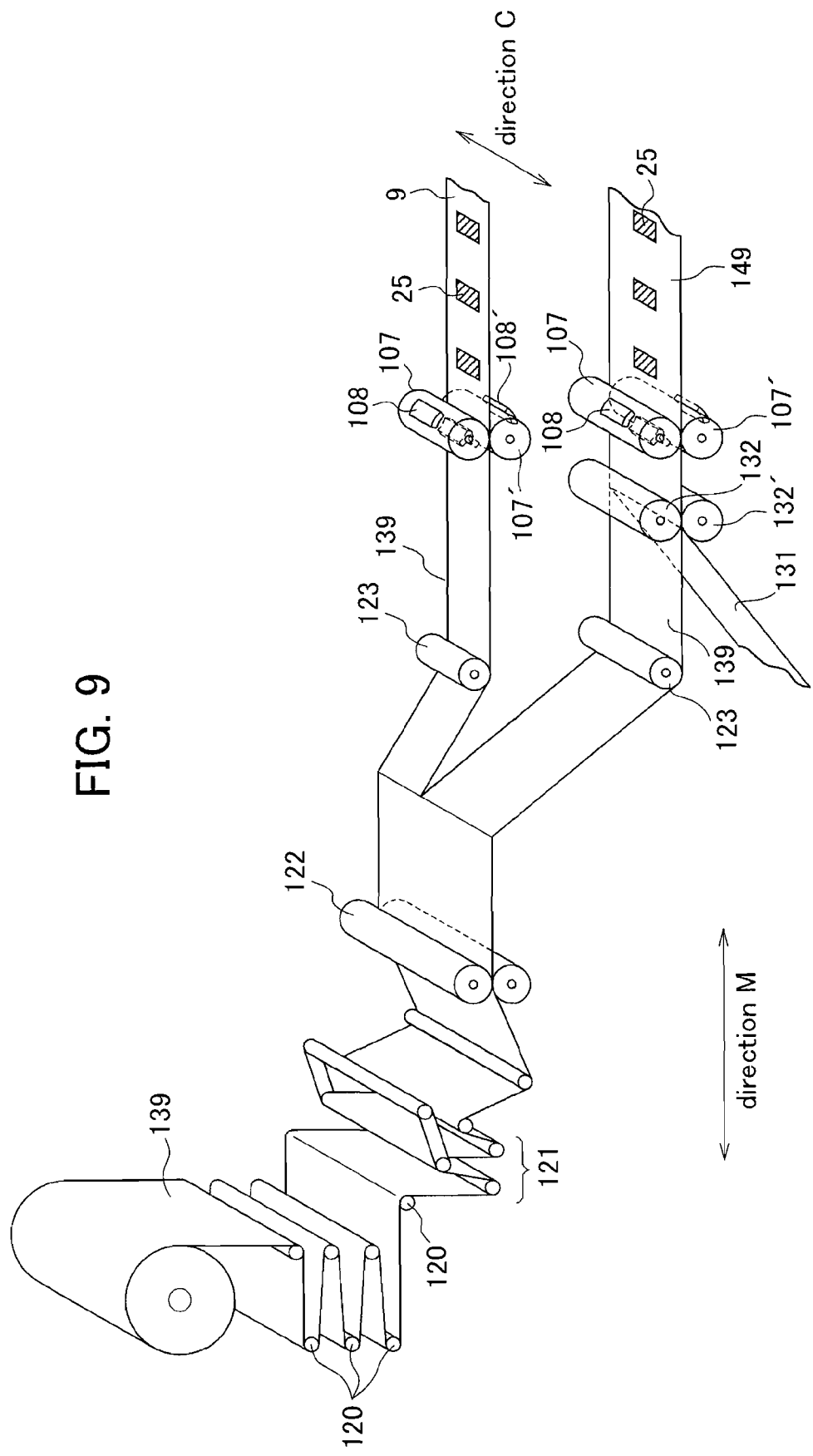
FIG. 9 is a diagram illustrating another stretchable non-woven fabric manufacturing process in the first embodiment of the present invention.

FIG. 1 is a perspective view showing a disposable diaper 1 in the first embodiment of the present invention. FIG. 2 is a developed view showing the disposable diaper 1 in the expanded state. FIG. 3 is an exploded perspective view showing the disposable diaper 1. FIG. 4 is a sectional view taken along the line Y-Y in FIG. 2. FIG. 5 is a sectional view taken along the line X-X in FIG. 2. FIG. 6A is a cross-sectional view showing a low-stretchability region. FIG. 6B is a partially enlarged view of the low-stretchability region. FIG. 7 is a diagram illustrating a manufacturing process of a stretchable non-woven fabric 9. FIG. 8 is a diagram illustrating a manufacturing process of a disposable diaper 1. FIG. 9 is a diagram illustrating another manufacturing process of a stretchable non-woven fabric 9.

1. Embodiment

1-1. Overall Configuration of Absorbent Article

The general configuration of the disposable diaper of the present invention is described with regard to a disposable diaper 1 in the present embodiment. In the present embodiment, it is assumed that the side of the disposable diaper facing a wearer's body is a skin-contacting side, and the side opposite to the skin-contacting side is a skin non-contacting side.

As shown in FIG. 1, the disposable diaper 1 according to the present embodiment has a chassis 2 forming the outer body and waistline of the disposable diaper 1 at wearing. As shown in FIG. 2, the chassis 2 includes the front trunk region 21 facing the wearer's abdomen, the rear trunk region 22 facing the wearer's back and the crotch 23 arranged therebetween.

The chassis 2 is composed of a base sheet 9c formed with a non-stretchable seat, and stretchability non-woven fabrics 9a and 9b. Specifically, the chassis 2 is constructed by arranging the stretchable non-woven fabrics 9a and 9b in the front trunk region 21 and the rear trunk region 22 of the base sheet 9c on a skin non-contacting side thereof. The stretchable non-woven fabrics 9a and 9b are composed of a thermoplastic fiber and a heat-adhesive fiber having a lower melting point than that of the thermoplastic fiber. In other words, the front trunk region 21 and the rear trunk region 22 of the chassis 2 are composed of a base sheet 9c and a stretchable composite sheet consisting of stretchable non-woven fabrics 9a and 9b.

As shown in FIG. 4, which is a sectional view taken along the line Y-Y in FIG. 2, the low-stretchability region 25 is formed in at least a portion of the stretchable non-woven fabrics 9a and 9b. Specifically, the low-stretchability region 25, in which the stretchability of the stretchable non-woven fabrics 9a and 9b is lower than that of other regions, is formed in at least a portion of the stretchable non-woven fabrics 9a and 9b which overlap an absorbent body 4 in a thickness direction TD. Formation of the low-stretchability region 25 is described later in detail. This lowers the stretchability of the stretchable non-woven fabrics 9a and 9b, in a region having the low-stretchability region 25 formed, of a portion overlapping an absorbent body 4 in a thickness direction TD, and can inhibit the formation of wrinkles on the absorbent body 4, especially on the outer edge thereof, due to the stretchability of the stretchable non-woven fabrics 9a and 9b.

The disposable diaper 1 is formed in a so-called shorts-shape by superimposing and joining the front trunk region 21 and the rear trunk region 22, by predetermined junctions 24a and 24b formed on both side edges thereof.

Specifically, as shown in FIG. 2, the disposable diaper 1 is formed in a shorts-shape by adhesively laminating the junction 24a of the front trunk region 21 and the junction 24b of the rear trunk region. Then, a pair of side edges 95 becomes a pair of leg openings 7 and 7. Then, both edges in the lengthwise direction LD of FIG. 2 (a front edge 91 and a back edge 93) become a trunk opening 8.

The edge of the leg openings 7 and 7 may be arranged with a leg gather sheet 73 and a predetermined elastic member in the entirety or in a portion thereof. Specifically, a plurality of filiform or band-shaped elastic members 72 can be arranged along side edges of the leg gather sheet 73 which is arranged along side edges of the absorbent body 4 (described later). Leg gathers 71 and 71 as shown in FIG. 1 are thus provided.

In addition, as shown in FIGS. 2 to 5, a stretchable crotch sheet 74 can be arranged along side edges of the crotch 23 in the chassis of the disposable diaper 1. Specifically, the crotch sheet 74 is constituted of a stretchable non-woven fabric, and adhesively arranged to a side edge 95 of a crotch area of the base sheet 9c on a skin non-contacting side thereof. In other words, the crotch sheet 74 and the base sheet 9c form a composite sheet.

Similarly, the edge of the trunk opening 8 may be arranged with a predetermined elastic member. Specifically, as shown in FIG. 2, a plurality of filiform or band-shaped elastic members 82 is arranged along a front edge 91 of the front trunk region 21. Similarly, a plurality of filiform or band-shaped elastic members 82 can be arranged along a rear edge 93 of the rear trunk region 22. The waist gathers 81 as shown in FIG. 1 are thus provided.

As shown in FIG. 3, the disposable diaper 1 includes a vertically long liquid permeable surface sheet 3 disposed on the skin-contacting side constituting a surface layer, a vertically long liquid retentive absorbent body 4 disposed between the surface sheet 3 and the base sheet 9 constituting an absorbent layer, a vertically long liquid impermeable back sheet 5 disposed on the skin non-contacting side constituting a back layer and a crotch outer sheet 6 disposed on the skin non-contacting side of the back sheet 5 which is the outermost layer of the disposable diaper 1. The surface sheet 3, the absorbent body 4, the back sheet 5 and the crotch outer sheet 6 are placed in the lengthwise direction LD from the front trunk region 21 through the rear trunk region 22 via the crotch 23. Thus, discharged matter from the excretory part, such as urine, passes through a liquid permeable region of the surface sheet 3, and is then absorbed by the absorbent body 4. Since the back sheet 5 disposed on the skin non-contacting side is liquid impermeable, the discharged matter such as urine can be absorbed by the absorbent body 4 and retained as is, without reaching the crotch outer sheet 6 and the skin non-contacting surface thereof.

1-2. Chassis

As shown in FIGS. 1 to 5, the chassis 2 includes the front trunk region 21 facing the wearer's abdomen, the rear trunk region 22 facing the wearer's back and the crotch 23 arranged therebetween. The front trunk region 21, the crotch 23, and the rear trunk region 22 are arranged in this order from one end to the lengthwise direction LD.

The chassis 2 is composed of a base sheet 9c, which is a non-stretchable sheet, and stretchable non-woven fabrics 9a and 9b arranged in the front trunk region 21 and the rear trunk region 22, respectively. In other words, the front trunk region 21 and the rear trunk region 22 of the chassis 2 are composed of a composite sheet, and the crotch 23 is composed of a portion of the base sheet 9c. The base sheet 9c is preferably consisted of, for example, a non-stretchable non-woven fabric manufactured by a spun-bond process.

The length of the chassis 2 in the width direction WD is preferably, for example, in the range of 300 to 1000 mm, and the length in the width direction WD of the front trunk region 21 in the front edge 91 is preferably in the range of 300 to 1000 mm. The length of the chassis 2 in the lengthwise direction LD is preferably in the range of 300 to 1000 mm. Especially with adult disposable diapers, the length of the chassis 2 in the width direction WD is preferably in the range of 450 to 900 mm when the front trunk region 21 or the rear trunk region 22 is extended, and the length thereof in the lengthwise direction LD is preferably in the range of 600 to 900 mm.

The length of the crotch 23 in the chassis 2 in the lengthwise direction LD is preferably in the range of 250 to 450 mm.

In addition, a side edge 95 is formed on the chassis 2 by a substantially U-shaped slit (refer to 77 of FIG. 8) of which the apex is substantially in the center in the width direction. By the presence of the slit, when the chassis 2 is formed in a shorts-like shape by binding the front trunk region 21 and the rear trunk region 22 by the junctions 24a and 24b, the side edge 25 forms leg openings 7 and 7. Simultaneously, the front edge 91 of the front trunk region 21 and the rear edge 93 of the rear trunk region 22 form a trunk opening 8.

1-3. Stretchable Non-Woven Fabric

As shown in FIGS. 3 to 5, stretchable non-woven fabrics 9a and 9b are arranged on a skin non-contacting side of the front trunk region 21 and the rear trunk region 22 of the base sheet 9c. The stretchable non-woven fabrics 9a and 9b are produced by forming a low-stretchability region 25 (described later) on an elasticized non-woven fabric 19, which is a stretchable non-woven fabric, on a portion overlapping the absorbing body 4 in a thickness direction when the stretchable non-woven fabrics 9a and 9b are placed on the base sheet 9c.

The elasticized non-woven fabric 19 is composed of a stretchable thermoplastic fiber and a heat-adhesive fiber having a lower melting point than that of the thermoplastic fiber. The elasticized non-woven fabric 19 is a stretchable non-woven fabric which is significantly elasticized by gear-drawing a non-stretchable (non-elasticized) non-woven fabric 18 composed of the abovementioned fibers, having little stretchability before the elasticization (see FIG. 7).

Examples of the stretchable thermoplastic fiber include a urethane fiber and a polyester fiber having stretchability. In addition, examples of the heat-adhesive fiber include polypropylene, polyethylene, polyethylene terephthalate and polybutylene terephthalate.

An example of a mixture ratio (in mass ratio) of the thermoplastic fiber and the heat-adhesive fiber is 30:70 to 70:30. With a mixture ratio of the thermoplastic fiber greater than 70%, the intended lowering of stretchability cannot be obtained. On the contrary, with a mixture ratio of the heat-adhesive fiber 129 greater than 70%, an intended stretching force cannot be obtained due to strain of the stretchable non-woven fabrics 9a and 9b.

The elasticized non-woven fabric 19 is obtained by gear-drawing a non-elasticized non-woven fabric 18 composed of such fibers having little stretchability. In the gear drawing process, as shown in FIG. 7, the non-elasticized fiber 18 is pressed by a pair of gear rollers 102 and 102' to extend heat-adhesive fibers and obtain stretchability.

Although the stretchable thermoplastic fiber contracts to an original fiber length after the gear drawing process, the heat-adhesive fiber maintains the extended fiber length, at least partially, after the processing. The extended fiber length is an extension allowance of the elasticized non-woven fabric.

The stretchability of the elasticized non-woven fabric itself, indicating the range of the length extended, is preferably 20 to 200%. The stretchable direction of the elasticized non-woven fabric 19 can be either the MD (machine direction) thereof or the CD (direction orthogonal to the machine direction) thereof, or both the MD and CD. The stretchable direction imparted to the non-elasticized non-woven fabric 18 by the gear drawing process can be determined by applications of the absorbent articles; however, in the present embodiment, the elasticized non-woven fabric 19 has stretchability in at least the MD (in the width direction WD of the disposable diaper 1).

A measuring method of stretchability of the elasticized non-woven fabric 19 is hereinafter described. The following equation is applied. Here, Y is a length of a target sheet (in this case, the elasticized non-woven fabric 19) extended to a maximum extent, and y is a length of the target sheet contracted by itself thereafter.

$$\text{Stretchability} = Y/y * 100 - 100$$

Moreover, the stretchability can be calculated by: marking on the target sheet at regular intervals (e.g., 100 mm) in the stretching direction; measuring the distance between marks when the target sheet is extended to a maximum extent; and then applying the abovementioned equation.

Then, in a portion of the elasticized non-woven fabric 19, the low-stretchability region 25 is formed having lower stretchability than other portions of the elasticized non-woven fabric 19. Stretchable non-woven fabrics 9a and 9b are thus formed.

The basis weight of the base sheet 9c, which is a non-stretchable non-woven fabric, is preferably in the range of 10 to 50 g/m$^2$; the basis weight of the non-elasticized non-woven fabric 18, which is a non-elasticized original non-woven fabric for the stretchable non-woven fabric, is preferably in the range of 20 to 100 g/m$^2$; and the basis weight of the elasticized non-woven fabric 19, for forming the stretchable non-woven fabrics 9a and 9b, is preferably in the range of 20 to 130 g/m$^2$.

1-4. Low Stretchability Region

The low-stretchability region 25 is a region formed by a process of lowering stretchability in a portion of the elasticized non-woven fabric 19, having a lower stretchability than other portions of the elasticized non-woven fabric 19. Specifically, the low-stretchability region 25 is formed in a portion which is arranged substantially in a center in the width direction WD of each of the front trunk region 21 and the rear trunk region 22 when the elasticized non-woven fabric 19 is disposed thereto, and which at least overlaps the absorbent body 4 in a thickness direction TD.

The length of the low-stretchability region 25 in a width direction WD is at least half of the length in the width direction of the absorbent body 4, and more preferably two-thirds thereof. Additionally, it is preferably in the range of 7 to 40%, more preferably in the range of 12 to 30% of the length in the width direction WD of the front trunk region 21 or the rear trunk region 22 which is extended to a maximum extent after expanding the disposable diaper 1. In a case in which the length in the width direction WD of the low-stretchability region 25 is less than 7%, the length in the width direction WD of the low-stretchability region 25 may be less than half of the length in the width direction WD of the absorbent article 4. Moreover, wrinkles may be developed depending on a method of joining the absorbent article 4 and the chassis 2. Meanwhile, in a case in which the length in the width direction WD of the low-stretchability region 25 is more than 40%, the flexible range of the low-stretchability region 25 in a trunk region may be insufficient and the comfort during wearing may be decreased. It should be noted that, although the low-stretchability region 25 is preferably formed in the entirety of a region in the front trunk region 21 and the rear trunk region 22 which overlaps the absorbent body 4 in the thickness direction TD, the arrangement is not limited thereto and can be formed along a side edge in the lengthwise direction LD of the absorbent body 4.

The length of the low-stretchability region 25 in a width direction WD in an extended state is preferably in the range of 60 to 250 mm. For manufacturing adult disposable diapers, the length in the width direction WD of the elasticized non-woven fabric 19 in an extended state, arranged in both of the side portion in the width direction WD of the low-stretchability portion 25, is preferably in the range of 100 to 420 mm for each side, and more preferably in the range of 200 to 300 mm.

The length of the low-stretchability region 25 in a lengthwise direction LD is preferably not shorter than the length in a lengthwise direction LD of the absorbent body 4 which is overlapping the absorbent body 4 in a thickness direction TD in at least the front trunk region 21 or the rear trunk region 22. Specifically, in the range of 60 to 250 mm for each side can be exemplified. In a case in which the length is shorter than 60 mm, the low-stretchability region 25 may be unable to sufficiently cover the length in a lengthwise direction LD of a portion in which the absorbent body 4 overlaps the stretchable non-woven fabrics 9a and 9b in a thickness direction TD.

The tensile strength of the low-stretchability region 25 in a stretchable direction is preferably at least 3N/50 mm. In a case in which the tensile strength is lower than 3N/50 mm, the low-stretchability region 25 may fracture in a manufacturing process of a disposable diaper 1, or may be torn apart during wearing of the disposable diaper 1.

The measuring method of the tensile strength and the fracture elongation is described hereinafter. A test piece is obtained by cutting the low-stretchability region 25 in the contracted state by 50 mm, then a tensile test is conducted using an autograph tensile test machine (AG-1KNI manufactured by Shimadzu Corporation): Holding both of the ends of the test piece by the machine with a grip spacing (the length of the test piece except the portion held by the machine) of 100 mm, the test piece is stretched at a speed of 100 mm/min until the test piece is fractured and the full strength is measured at the moment of fracture (the tensile strength). The elongation at the moment of fracture is also measured (the fracture elongation).

In a process of lowering stretchability, stretchable non-woven fabrics 9a and 9b are formed by: heating the elasticized non-woven fabric 19 in the extended state at a predetermined temperature; and then pressurizing in a thickness direction TD a predetermined region thereof to obtain a low-stretchability region. Specifically, a region, which at least overlaps the absorbent body 4 in the thickness direction TD when the elasticized non-woven fabric 19 (as stretchable non-woven fabrics 9a and 9b) is arranged in the front trunk region and the rear trunk region of the disposable diaper 1, of the elasticized non-woven fabric 19 in the extended state is pressurized at a temperature at which the heat-adhesive fiber can be deformed.

The pressurizing and the heating can be selected appropriately from conventionally known methods, for example, a heat embossing method pressurizing and heating at the same time, a method of heating by hot air and then pressurizing by a roller, and a method of generating heat by ultrasonic waves and pressurizing by a roller.

A fusion structure of the heat-adhesive fibers 129 fused to each other is thus formed by heating and pressurizing the elasticized non-woven fabric 19, which is elasticized by a gear drawing process, in the extended state.

In particular, as shown in FIG. 6A, the low-stretchability region 25 is formed to have the length in a thickness direction TD which is shorter (thinner) than that of other regions in the stretchable non-woven fabric, by the process of lowering stretchability. In other words, the process of lowering stretchability (described later) pressurizes the low-stretchability region 25 at a predetermined pressure.

Additionally, the low-stretchability region 25 is formed to have a distance between fibers shorter than that of other regions, by introducing the stretchable non-woven fabric 9 to a process of lowering stretchability in the extended state. The low-stretchability region 25 is formed to have a density higher than that of other regions, by pressurizing with heat processing in the process of lowering stretchability.

As shown in FIG. 6B, the heat-adhesive fibers 129 in the low-stretchability region 25 are fused to each other by heat to form a fusion structure, by being introduced to the process of lowering stretchability in the extended state. Therefore, a stretching motion of the thermoplastic fiber 119, being extended or contracted, is inhibited by the fusion structure of the heat-adhesive fiber 129. This limits the stretchability of the low-stretchability region 25.

The stretchability of the low-stretchability region 25 in the stretchable non-woven fabrics 9a and 9b is preferably not more than 25%, and more preferably not more than 15%. The stretchability of the other regions in the stretchable non-woven fabrics 9a and 9b is preferably at least 30%. The stretchability of the stretchable non-woven fabrics 9a and 9b can be measured as described above.

Additionally, a ratio of the length in the width direction WD after extending and contracting, to the initial length in the width direction WD (ductility) of the stretchable non-woven fabrics 9a and 9b, that are arranged in the front trunk region 21 and the rear trunk region 22 of the disposable diaper 1, is preferably not more than 15%.

1-5. Absorbent Body

As shown in FIGS. 2 to 5, the absorbent body 4 is liquid retentive and formed in a substantially elongated shape. It should be noted that the term "substantially elongated"

includes a generally rectangular shape having a lengthwise direction LD and width direction WD. Moreover, the term includes a shape in which a portion of both sides in the lengthwise direction LD is tapered to the center in the lengthwise direction LD or may bulge in the direction opposite the center. Specifically, the absorbent body 4 includes an absorbent body that is different in length in the width direction WD in a portion in the lengthwise direction LD.

The absorbent body 4 may be arranged in the state of being covered with tissues (not shown) or a hydrophilic non-woven fabric 41. When covered with a hydrophilic non-woven fabric, the absorbent body 4 may be configured without application of the surface sheet 3 or with only partial application thereof. This allows for a reduction in manufacturing cost.

The stiffness of the absorbent body is preferably in the range of 0.01 to 0.6N/cm, for a comfort of a crotch and a trunk region during wearing. In a case in which the stiffness is less than 0.01N/cm, wrinkles can be developed on the absorbent body 4 itself. The stiffness can be measured using conventionally known devices by the Taber method.

The length of the absorbent body 4 in a width direction WD is preferably in the range of 120 to 250 mm. This is because the length in a width direction WD of the low-stretchability region 25 is preferably in a range of 10 to 30% of the length in a width direction WD of the disposable diaper 1. This is also because, in a case in which the length in the width direction of the low-stretchability region 25 is shorter than 120 mm, it is difficult to obtain a required absorbing property, and in a case in which the length is longer than 250 mm, it is difficult to obtain a required flexible range for a trunk region.

The absorbent body 4 and the liquid-permeable surface sheet 3 arranged on a skin-contacting side thereof are adhesively joined with a hot melt adhesive. In addition, a skin non-contacting surface of the absorbent article 4 and a base sheet 9 are adhesively joined using a hot-melt adhesive. To a portion of the absorbent article 4 overlapping the stretchable non-woven fabrics 9a and 9b arranged on the base sheet 9c in a thickness direction TD, a hydrophilic non-woven fabric 41, which wraps the absorbent article 4, is preferably joined at least by the peripheral end thereof. The coating patterns of the hot melt adhesive include controlled seam coating, slot coater coating, spiral coating, curtain coater coating, summit-gun coating and the like, for example. The basis weight of the hot-melt adhesive in the hot-melt adhesion is preferably in the range of 2 to 15 g/m$^2$.

1-6. Manufacturing Method 1-6-1. Overview

A manufacturing method of the disposable diaper 1 is described with reference to FIGS. 7 and 8. The disposable diaper 1 is manufactured by forming stretchable non-woven fabrics 9a and 9b, forming a composite sheet by adhesively joining the stretchable non-woven fabrics 9a and 9b to a base sheet 9c which is a non-stretchable non-woven fabric, and joining components of the disposable diaper 1 to the composite sheet.

To obtain the stretchable non-woven fabrics 9a and 9b, firstly, a non-elasticized non-woven fabric 18, constituted of a thermoplastic fiber and a heat-adhesive fiber, is processed by a gear drawing process to obtain an elasticized non-woven fabric 19. Then, a low-stretchability region 25 is formed by processing at least a portion of the elasticized non-woven fabric 19 by a process of lowering stretchability.

A front trunk region 21 or a rear trunk region 22 is formed by joining the stretchable non-woven fabrics 9a and 9b thus obtained, in the extended state, to a base sheet 9c. Subsequently, a crotch outer sheet 6, a liquid impermeable back sheet 5 and a crotch sheet 74 are joined to a skin non-contacting side of the base sheet 9c; a leg gather sheet 73, an absorbent body 4, and a liquid permeable surface sheet 3 are joined to a skin-contacting side of the base sheet 9c; then a waist gather 81 is formed to obtain the disposable diaper 1.

1-6-2. Manufacturing Method of Stretchable Non-Woven Fabric

A manufacturing method of the stretchable non-woven fabrics 9a and 9b is described with reference to FIG. 7. Firstly, a non-elasticized non-woven fabric 18 (non-gear drawn) is unreeled from an original fabric roll 101.

The elasticized non-woven fabric 19 is obtained by gear-drawing the unreeled non-elasticized non-woven fabric 18. Specifically, the non-elasticized non-woven fabric 18 is inserted between a pair of gear rollers 102 and 102' with a pair of toothed regions 103 engaging each other. The toothed region 103 extends a heat-adhesive fiber. The stretching direction can be selected from MD, CD, and a combination thereof, in accordance with an intended use. To obtain bi-directional stretchability, the non-elasticized non-woven fabric 18 can be gear-drawn twice in different directions. In other words, after obtaining stretchability in any one of MD and CD, the non-elasticized non-woven fabric 18 can be gear-drawn for the second time in the other direction. In the present embodiment, the elasticized non-woven fabric 19 has stretchability in at least the MD.

Subsequently, the elasticized non-woven fabric 19 is extended in the MD, for example by 1.8 times, by a pair of rollers 104 and 105. Here, the length in the CD of the elasticized non-woven fabric 19 inserted between the pair of rollers 104 and 105 becomes shorter than that before extending, by being extended in the MD, thus the elasticized non-woven fabric 19 is in a state of so-called neck in.

Then, the elasticized non-woven fabric 19 is widened by a widening process by a pair of widening roller 106 and 106'. This process widens the elasticized non-woven fabric 19 being narrower in the CD by being extended in the MD, being in a state of so-called neck in. To widen the elasticized non-woven fabric 19 to neck in, the length in the CD of the elasticized non-woven fabric 19 is read by a sensor 110 arranged before the widening rollers 106 and 106', and the length is adjusted to a predetermined length by the pair of widening rollers 106 and 106' in two phases. Subsequently, the elasticized non-woven fabric 19 being extended and widened is inserted to a heat embossing roller 107, which is a process of lowering stretchability.

A pair of heat embossing rollers 107 and 107' is a principal unit of the process of lowering stretchability of the elasticized non-woven fabric 19. The heat embossing rollers 107 and 107' is a pair of rollers having a compressing unit 108 which lowers stretchability of the elasticized non-woven fabric 19. The compressing unit 108 is arranged on each of the heat embossing rollers 107 and 107', and arranged to engage each other. The compressing unit 108 projects a convex shape from the circumference of heat embossing rollers 107 and 107'. A plurality of compressing units 108 is arranged along the circumference of the heat embossing rollers 107 and 107'. The interval between the plurality of compressing units 108 arranged along the circumference of the heat embossing rollers 107 and 107' is the interval (pitch) between the low-stretchability regions 25 formed on the stretchable non-woven fabric 9. In other words, compressing units 108 are arranged on the heat embossing rollers 107 and 107' in accordance with the interval (pitch) between the low-stretchability regions 25 formed on the stretchable non-woven fabric 9. A pitch between the lateral portion in the direction of motion of a compressing unit 108 and the lateral portion in the direction of motion of another compressing unit 108, neighboring thereto in the direction of motion, is preferably equal to the length in a width direction WD of the chassis 2.

The temperature of the compressing unit 108 is preferably in the range of 90 to 130° C. In a case in which the temperature of the compressing unit 108 is lower than 90° C., the heat-adhesive fibers cannot be fused to each other and stretchability cannot be lowered. On the other hand, in a case in which the temperature of the compressing unit 108 exceeds 130° C., the heat-adhesive fiber is adhered to the roller and the compressing unit 108 and the stretchable non-woven fabric 9 can be damaged.

The elasticized non-woven fabric 19 is preferably heat-processed by, for example, hot air or ultrasonic waves before being inserted between the heat embossing rollers 107 and 107' This makes the fibers constituting the elasticized non-woven fabric easy to deform. The temperature for the heat-processing is preferably in the range of 40 to 80° C.

The linear pressure of the heat embossing rollers 107 and 107' is preferably in the range of 30 to 1000 kgf/cm. Linear pressure lower than 30 kgf/cm is insufficient to cut off fibers, and linear pressure exceeding 1000 kgf/cm burdens the unit and can shorten the life of the rollers by damaging a surface coating and the like of the sheet for avoidance of an entanglement therewith.

The finishing by the compressing portion 108 includes, for example, a matt finish, satin finish and sandblast finish. By choosing the finishing of the compressing portion 108, the remaining stretchability and the surface texture of the low-stretchability portion 25 can be adjusted to some degree. Specifically, by changing a finishing, forming the surface of the stretchable non-woven fabric 9 into a film or becoming too rigid can be avoided. For example, with a matt finish, the remaining stretchability is 0% and the surface becomes rigid, and with a satin finish, an improved texture with a lowered remaining stretchability can be obtained by a delicate concavo-convex structure on the surface.

The stretchable non-woven fabric 9 is thus formed by a process of lowering stretchability. To arrange the stretchable non-woven fabric 9 along a front trunk region 21 and a rear trunk region 22 of the disposable diaper 1, the stretchable non-woven fabric 9 is brought into a production line for the disposable diaper 1 (described later) to be extended in the MD. The stretchable non-woven fabric 9 is narrower in the CD by being extended to the MD, being in a state of so-called neck in. Therefore, the length in the CD is preferably adjusted to a predetermined length by the pair of the widening rollers 109 and 109' in two phases, by reading the length in CD of the stretchable non-woven fabric 9 by a sensor 111. The length in CD after the widening is preferably adjusted to be in the range of 85 to 100% of the length before the state of neck in (the length in the CD of the non-elasticized non-woven fabric 18).

In the present embodiment, the low-stretchability region 25 is arranged substantially in a center of the elasticized non-woven fabric 19. In addition, the low-stretchability region 25 can be formed in stretchable non-woven fabrics 9a and 9b, across in a width direction WD within regions in which waist gathers 81 are formed, that are arranged on a front edge 91 of the front trunk region 21 and on a rear edge 93 of the rear trunk region 22. Moreover, the low-stretchability region 25 can be formed in stretchable non-woven fabrics 9a and 9b, across in a width direction WD along the crotch 23-side edge of the front trunk region 21 and the rear trunk region 22.

1-6-3. Manufacturing Method of Disposable Diaper

A manufacturing method of the disposable diaper 1 is described with reference to FIG. 8. The following manufacturing method is merely an example and other methods may be employed.

First, a crotch sheet 74 composed of the elasticized non-woven fabric 19 is adhered by a hot-melt adhesive to a side (a skin non-contacting side of the disposable diaper 1) of the base sheet 9c (chassis 2) which is a non-stretchable non-woven fabric (FIG. 8(A)). The elasticized non-woven fabric 19 is adhered being cut into a predetermined dimension and extended by 1.9 times.

Then, a back sheet 5 and a crotch outer sheet 6, which are liquid-impermeable sheets, are sequentially joined to the base sheet 9c (chassis 2) by a hot-melt adhesive on a skin non-contacting side of the crotch sheet 74 (FIG. 8(B)).

The stretchable non-woven fabric 9 produced as described above is divided into stretchable non-woven fabrics 9a and 9b to be arranged in the front trunk region 21 and the rear trunk region 22, being extended in the MD by 1.8 times of the initial length (length in the MD of a non-elasticized non-woven fabric 18) and being divided in the CD by a incision along the MD (FIG. 8(C)). Then the stretchable non-woven fabrics 9a and 9b are joined to the front trunk region 21 and the rear trunk region 22, on a skin non-contacting side of the base sheet 9c (FIG. 8(D)). A chassis 2 is thus formed. The chassis 2 has stretchability in a width direction (WD) in the front trunk region 21 and the rear trunk region 22.

Additionally, a stretchable member 82 (not shown) is arranged in the vicinity of both of the sides in the CD of the chassis 2 along the MD, and a waist gather 81 is formed by folding back both of the side portions to a skin non-contacting side (FIG. 8(E)).

A crotch sheet 74, a back sheet 5, a crotch outer sheet 6 and stretchable non-woven fabrics 9a and 9b are joined to the chassis 2, and then the chassis 2 is cut along the CD at a predetermined length in the MD. Furthermore, a slit 77 is made on each side of the chassis 2 which is cut out, to form a leg opening 7 and 7 (FIG. 8(F)).

A leg gather sheet 73 for forming a leg gather 71 is firstly joined to a skin-contacting side of the chassis 2 by hot-melt adhesion (FIG. 8(G)). In this case, preferably only the crotch 23-side of the leg gather sheet is joined and the other end is made to be a free end. Then, on a skin-contacting side of the leg gather sheet 73, an absorbent body wrapped in a hydrophilic non-woven fabric 41 and a liquid permeable surface sheet 3 are adhesively joined sequentially to the crotch 23 (FIG. 8(H)).

Finally, a disposable diaper 1 is formed in a shorts-like shape by folding a chassis 2 with a skin-contacting side inside, and joining the front trunk region 21 and the rear trunk region 22 of the chassis 2 by the junctions 24a and 24b (FIG. 8(I)).

According to the present embodiment, by forming a low-stretchability region 25, a region having lower stretchability than that of the other portion of the stretchable non-woven fabric 9, in a portion of the stretchable non-woven fabric 9 overlapping an absorbent body 4 in a thickness direction TD, the formation of wrinkles on the absorbent body 4 arranged thereon due to the stretchability of the stretchable non-woven fabric 9, can be inhibited.

Additionally, the low-stretchability region 25 has an unshrunk portion on which the absorbent body 4 is arranged, which can support the absorbent body 4 with a plane surface. This can inhibit the formation of wrinkles on and the twisting of the absorbent body 4 during wearing of the disposable diaper 1.

Thus, the absorbent body 4 can be kept flat and can have a larger absorbing dimension than in a case in which the absorbent body 4 has wrinkles. In addition, by inhibiting the formation of interspaces due to wrinkles, the absorbent body 4 can be in close contact with the wearer's body. This prevents the discharged matter from leaking out due to unnecessary deformation of the absorbent body 4.

Moreover, the comfort during wearing can be improved by inhibiting twisting or rolling up of the absorbent body 4. The high stiffness of the absorbent body 4, which deteriorates comfort during wearing, is thus not necessary to avoid twisting of the absorbent body 4.

Furthermore, twisting or rolling up of a junction between the stretchable non-woven fabrics 9a and 9b and the crotch outer sheet 6 of the disposable diaper 1 can be inhibited and the appearance thereof can be improved by inhibiting the formation of wrinkles on the absorbent body 4.

2. Variation

Variations according to the present invention are described hereinafter. Variation 1 is a variation of the manufacturing method of the stretchable non-woven fabric 9 and Variation 2 is a variation of the stretchable non-woven fabric 9. The following variations, unless otherwise noted, are similar to the foregoing embodiment, and the same reference numerals have been retained for similar parts.

2-1. Variation 1

Variation 1 is described hereinafter with reference to FIG. 9. Variation 1 is a variation of the manufacturing method of the stretchable non-woven fabric 9. The stretchable non-woven fabric 9 of the present invention can be produced by lowering stretchability of a typical stretchable non-woven fabric 139, which is formed without a gear-drawing process, by a process of lowering stretchability.

A stretchable non-woven fabric 139, with an extensible range of 100%, unreeled from an original fabric roll 101 is introduced to a tension controller 121 while being gradually extended by a roller 120. The stretchable non-woven fabric 139 is thus extended to, for example, 110% of the initial length thereof in the MD by the tension controller 121.

The stretchable non-woven fabric 139 is further extended to, for example, 160% of the initial length thereof in the MD, while being gradually extended by rollers 122 and 123. The stretchable non-woven fabric 139 can be cut in the MD in advance by a slitter (not shown), so that the stretchable non-woven fabric 139 can be arranged to a front trunk region 21 and a rear trunk region 22.

Subsequently, the stretchability of the stretchable non-woven fabric 139, being extended to about 160%, is partially lowered by a pair of heat embossing rollers 107 and 107'. A stretchable non-woven fabric is thus obtained.

2-2. Variation 2

Variation 2 is described hereinafter with reference to FIG. 9. Variation 2 is a variation of the stretchable non-woven fabric 9.

The stretchable non-woven fabric 9 of Variation 2 is obtained by joining a non-stretchable non-woven fabric 131 to the stretchable non-woven fabric 139 obtained as described above, before introducing the stretchable non-woven fabric 139 to the pair of heat embossing rolls 107. Subsequently, the stretchability of the stretchable non-woven fabric 9 is partially lowered by the pair of heat embossing rollers 107 and 107'. In other words, a composite sheet 132 is obtained by joining the stretchable non-woven fabric 139 and the non-stretchable non-woven fabric 131, then the composite sheet 132 is introduced to the pair of heat embossing rolls 107 to partially lower the stretchability thereof, and a stretchable composite sheet 149 is obtained.

3. Examples

Examples of the present invention are described hereafter. However, the following examples are provided for purposes of illustration only, and are not intended to limit the invention.

A non-elasticized non-woven fabric 18 was obtained by mixing a polyurethane fiber and a polypropylene fiber at a mixture ratio of 40:60, and then the non-elasticized non-woven fabric 18 was gear-drawn to obtain an elasticized non-woven fabric 19. The weight of the non-elasticized non-woven fabric 18 was 35 g/m$^2$ and the weight of the elasticized non-woven fabric 19 in the contracted state was 38.5 g/m$^2$.

Then, the elasticized non-woven fabric 19 extended by 1.8 times was introduced to a pair of heat-embossing rollers 107 and 107' heated to 115° C., and a low-stretchability region 25 was formed thereon by the pair of heat-embossing rollers 107 and 107' for a satin finish, thereby obtaining a stretchable non-woven fabric 9. The stretchable non-woven fabric 9 was joined to a base sheet 9c, which was a non-stretchable non-woven fabric, by a hot-melt adhesive to obtain a disposable diaper 1. The linear speed for producing the stretchable non-woven fabric 9 was 20 m/min, and the linear pressure of the heat embossing rollers 107 and 107' was 167 kgf/cm. The basis weight of the hot melt adhesive was 5 g/m$^2$, and the coating pattern thereof was spiral coating.

Examples 1 to 4 were obtained by producing the non-woven fabric 9 with different heat embossing patterns and temperatures, which are measured and compared for the fracture elongation, the tensile strength, and the surface state of the low-stretchability region 25.

The fracture elongation and the tensile strength were measured as described above.

The result is as shown in Table 1.

TABLE 1

| Example | Embossing Pattern | Depth of Pattern (mm) | Temperature of Heat Embossing (° C.) | Temperature of Flat Roller (° C.) | Remaining Stretchability | Tensile Strength (N/50 mm) | Surface State of Low-stretchability region |
|---|---|---|---|---|---|---|---|
| Example 1 | Matt (Blank) | — | 119 | 110 | 0% | 50.65 | Partially film-like, inferior texture |
| Example 2 | Sandblast | 0.008 | 118 | 110 | Less than 15% | 48.08 | Partially film-like, inferior texture |

TABLE 1-continued

| Example | Embossing Pattern | Depth of Pattern (mm) | Temperature of Heat Embossing (° C.) | Temperature of Flat Roller (° C.) | Remaining Stretchability | Tensile Strength (N/50 mm) | Surface State of Low-stretchability region |
|---|---|---|---|---|---|---|---|
| Example 3 | Sandblast | 0.03 | 121 | 106 | Less than 15% | 49.43 | Moderate |
| Example 4 | Satin | 0.09 | 115 | 120 | Less than 15% | 40.9 | Superior |
| Example 5 | Sandblast | 0.08 | 118 | 105 | More than 25% | 9.02 | Unacceptable texture with broken fibers |

According to Table 1, Example 4 had the optimum characteristics. Example 4 had a superior surface state and less preferable remaining stretchability. In addition, the surface of the low-stretchability region 25 was not turned into a film and kept the state of non-woven fabric. The tensile strength thereof was high enough to be used in an absorbent article. In contrast, Example 1 produced with matt finishing had remaining stretchability of nearly 0%, which indicates that the finish was the most effective. However, the surface state was somewhat film-like and deteriorates the appearance. Example 2 had remaining stretchability of less than 15% by virtue of the shallow embossing patterns; however, the surface state was somewhat film-like as with Example 1. Example 5 had a lower embossing rate than the other examples, and fibers were broken due to high pressure. This resulted in lowered tansile strength.

What is claimed is:

1. A stretchable non-woven fabric comprising:
a stretchable thermoplastic fiber;
heat-adhesive fibers having a lower melting point than that of the stretchable thermoplastic fiber; and
a low-stretchability region in a substantially central area in the width direction of the non-woven fabric,
wherein a stretchability is lowered to less than that of an area other than the central area by fusing at least the heat-adhesive fibers in the substantially central area to each other.

2. The stretchable non-woven fabric according to claim 1, wherein the low-stretchability region is air-permeable.

3. A method of manufacturing a stretchable non-woven fabric having a region in which stretchability is lowered in portions thereof, comprising:
a process of lowering a stretchability of a predetermined area in the stretchable non-woven fabric which includes a stretchable thermoplastic fiber and heat-adhesive fibers having a lower melting point than of the thermoplastic fiber, by fusing at least the heat-adhesive fibers to each other in the predetermined area,
wherein the process of lowering stretchability includes an operation of extending the stretchable non-woven fabric before fusing the heat-adhesive fibers to each other.

4. A method of manufacturing a stretchable composite sheet extending in each of a length direction and a width direction, the method comprising:
a non-woven fabric extending process wherein a stretchable non-woven fabric which includes a stretchable thermoplastic fiber and heat-adhesive fibers having a lower melting point than that of the thermoplastic fiber is stretched at a predetermined stretching rate selected from a range of 20 to 200%;
a composite sheet forming process wherein the non-woven fabric, which is extended in the non-woven fabric extending process, is adhesively laminated to a non-stretchable sheet to obtain the composite sheet; and
a process of lowering stretchability wherein stretchability of a substantially central area in a width direction of the composite sheet is lowered to less than that of an area other than the central area, after the non-woven fabric extending process, by fusing at least the heat-adhesive fibers in the predetermined area to each other.

5. An absorbent article having a width direction and a lengthwise direction orthogonal to the width direction, comprising:
a front trunk region;
a rear trunk region;
a chassis with a crotch arranged between the front trunk region and the rear trunk region; and
an absorbent body arranged along the longitudinal direction wherein at least a portion thereof overlaps the chassis in a thickness direction,
wherein a stretchable non-woven fabric comprising a stretchable thermoplastic fiber and heat-adhesive fibers having a lower melting point than that of the thermoplastic fiber is arranged in at least a portion of the chassis;
a low-stretchability region, formed in a substantially central area in the width direction of each of the front trunk region and the rear trunk region, and which at least overlaps the absorbent body in a thickness direction of the stretchable non-woven fabric, wherein the low-stretchability region has a lower stretchability than that of an area other than the central area in the width direction of each of the front trunk region and the rear trunk region, and
stretchability of a thermoplastic fiber in the low-stretchability region is inhibited by a fusion structure wherein the heat-adhesive fibers in the low-stretchability region are fused to each other.

6. The absorbent article according to claim 5, wherein the low-stretchability region is formed substantially in a center in the width direction of the front trunk region and the rear trunk region, and overlaps in the thickness direction at least both side edges in the width direction of the absorbent body.

7. The absorbent article according to claim 5, wherein the low-stretchability region is air-permeable.

8. The absorbent article according to claim 6, wherein the low-stretchability region is air-permeable.

* * * * *